US 8,154,224 B2

(12) United States Patent
Wedel

(10) Patent No.: US 8,154,224 B2
(45) Date of Patent: Apr. 10, 2012

(54) DISPLAY APPARATUS THAT CAN BE MOVED IN SPACE

(75) Inventor: Matthias Wedel, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 507 days.

(21) Appl. No.: 12/390,114

(22) Filed: Feb. 20, 2009

(65) Prior Publication Data

US 2009/0212719 A1 Aug. 27, 2009

(30) Foreign Application Priority Data

Feb. 25, 2008 (DE) .......................... 10 2008 010 990

(51) Int. Cl.
*H05B 37/02* (2006.01)
(52) U.S. Cl. ........................................ 315/363; 315/297
(58) Field of Classification Search ................. 315/363, 315/297, 313
See application file for complete search history.

(56) References Cited

U.S. PATENT DOCUMENTS

2005/0140941 A1* 6/2005 Maddock ..................... 353/119

FOREIGN PATENT DOCUMENTS

| DE | 196 23 188 C2 | 7/2000 |
| DE | 10 2006 024 512 A1 | 11/2007 |
| DE | 10 2007 057 757 A1 | 6/2008 |

OTHER PUBLICATIONS

German Office Action dated Oct. 31, 2008 with English translation.

* cited by examiner

*Primary Examiner* — Daniel D Chang
(74) *Attorney, Agent, or Firm* — Lempia Summerfield Katz LLC

(57) ABSTRACT

A medical examination or treatment facility comprising at least one display facility that can be moved in space is provided. The facility includes one or a plurality of lighting facilities arranged in a distributed manner to illuminate the space. It is possible to change the brightness and/or position of the individual lighting facilities automatically by a control or regulation facility as a function of a captured spatial position and/or orientation of the object, in particular of the display facility.

19 Claims, 3 Drawing Sheets

DISPLAY APPARATUS THAT CAN BE MOVED IN SPACE

This patent document claims the benefit of DE 2008 010 990.8, filed Feb. 25, 2008, which is hereby incorporated by reference.

BACKGROUND

The present embodiment relates to a system (facility) comprising an object to be viewed that can be moved in space. In particular, the present embodiments relate to a medical examination or treatment facility comprising at least one display facility that can be moved in space, as well as one or a plurality of lighting facilities arranged in a distributed manner to illuminate the space.

Medical examination or treatment facilities, for example, x-ray facilities or ultrasound facilities, have a display facility. The medical examination or treatment facilities may serve purely for examination purposes or optionally also for interventional treatment. A wide range of information relating to the examination or treatment may be displayed, for example, images that have just been recorded, may be displayed on a display facility. When the treating physician changes position during the examination or treatment, it is known that the display facility can be supported in a movable manner, for example, by suspending it from the ceiling by way of a suitable stand or securing it to a corresponding part of the facility by way of such a stand. The physician is able to move the display facility and orient the display facility so that the physician has an optimum view of the display facility, for example, a display unit, in another position.

With known examination or treatment facilities it is necessary to ensure the best possible illumination of the space, in other words particularly in the area where the examination or treatment is taking place. A plurality of lighting facilities are generally provided on the ceiling. The lighting facilities are mounted in a distributed arrangement, in order to be able to illuminate the examination or treatment area optimally from all sides. Although this ensures that medical personnel always have a well illuminated environment, problems arise in that it is not possible to exclude glare on the display facility, when the display facility is adjusted. In other words after the display facility has been adjusted, it is possible for it to be at such an angle to a lighting facility arranged on the ceiling or elsewhere that the lighting facility shines directly onto the display facility or its display field, resulting in reflection and glare. The user may not see the displayed information or can only see it in a very restricted manner or has to move again him/herself, in order to be able to capture the information and can be dazzled by way of the reflecting surface during his/her activity.

Facilities used in other fields also have similar problems, for example, facilities serving to present an object for exhibition. Such facilities frequently comprise a support, on which the object, for example, a vehicle, is arranged, which can be used to rotate the vehicle. Depending on the spatial orientation it is possible here for one or a plurality of lighting facilities to be reflected off the side of the vehicle, which is unpleasant. These problems also occur when exhibiting other objects.

SUMMARY AND DESCRIPTION

The present embodiments may obviate one or more of the problems or drawbacks inherent in the related art. For example, in one embodiment, a facility (system), such as a medical examination or treatment facility, largely excludes any possible restriction of the possibility of viewing the object or reading the display facility as a result of lighting while at the same time allowing the object and the display facility to be adjusted.

In one embodiment, a facility, such as a medical examination or treatment facility, may change the brightness and/or position of the one or each individual lighting facility automatically by way of a control or regulation facility as a function of the captured spatial position and/or orientation of the object, such as the display facility.

The operation of the one or each individual lighting facility may be controlled and/or regulated separately as a function of the spatial position and/or orientation of the object or display facility. The brightness or position of the one or a plurality of lighting facilities is monitored for any adjustment of the display facility, when the corresponding position/orientation of the object or display facility in space requires this, in order to avoid glare or reflection and therefore restriction of recognition of the information displayed for example. The actual position and/or actual orientation of the object or display facility is/are automatically captured so that information is available about how the object is oriented in space or how the display surface of the display facility, on which the information is displayed, is positioned or oriented in space. It is then possible to determine, when a plurality of lights arranged in a distributed manner are used, which lighting facility is arranged such and radiates in such a direction that possible reflection off the object surface or the display surface of the display facility results. The brightness of the lighting facility is then changed, for example, it is dimmed or even switched off, and/or its position is changed, so that its fundamental radiation direction changes. Changing the lighting facility is possible in a simple manner, for example, when the lighting facility is supported in a pivotable manner. The individual lighting and reflectors may be pivoted to some degree so that the radiation direction changes.

As a result of the change in brightness and/or position (e.g., both brightness and position can be changed simultaneously, if both variants are implemented), it is possible to avoid glare due to reflection off the object surface or the display surface of the display facility, regardless of how a movement controller positions the object in space or how the user positions the display facility in space according to requirements.

The defined actual brightness and/or the actual position of the individual lighting facilities is/are known, when operation of the individual lighting facilities is controlled or regulated by a control or regulation facility. Optimum brightness or position changes may be made to exclude glare.

The one lighting facility or the individual lighting facilities may be controlled or regulated by a central control or regulation facility. One benefit of the central control is that only one central facility is provided to adjust the brightness and/or position of all the lighting facilities. However, each lighting facility may have its own control or regulation facility.

The brightness may be changed continuously or in discrete steps (intervals) between a maximum brightness and a minimum brightness or a switched-off state. As a result, a large variation bandwidth, which allows optimum brightness adjustment depending on the given position of the display facility. The position of a lighting facility, which may be pivoted with its lighting device, and may be adjusted continuously or in discrete steps (intervals). The pivot angle may be $\leq 120°$, with a pivot angle from the interval between $45°$-$90°$ being sufficient for adequate adjustment.

The position and/or orientation of the object or display facility may be captured automatically, to which end a corresponding capture device for automatic capturing of the position and/or orientation is expediently provided. The capture device may communicate with the control or regulation facility/ies or can even be part of these, depending on the embodiment. Various alternatives are possible for the specific embodiment.

In one alternative embodiment, the capture device may be operable to capture the position and/or orientation. The capture device may be configured based on the spatial geometry of a support holding the object or a stand holding the display facility, such as an articulated stand. The position of a display facility supported by a stand is defined by the spatial geometry of the stand. When the spatial geometry is captured, the spatial geometry may be used directly to determine the spatial position and/or spatial orientation of the display facility. One or a plurality of sensors may be provided on the support or stand to capture a translatory or rotary stand movement. The sensors may be angle sensors in the region of swivel joints or linear sensors for telescopic guides. The sensors may allow any linear or rotary stand movement to be captured. The corresponding sensor signals are then transmitted, for example, to a central control facility. The central control facility may determine the position of the object or display facility and optionally activates one lighting facility or another correspondingly as a function of this position information.

As an alternative to using sensors on the stand, the spatial geometry and the spatial position of the object or display facility may be determine using camera systems. The stand or display facility, for example, may be recorded using two or more cameras. The spatial position of the display facility may be determined based on the camera positions and the corresponding representation of the display facility in the camera image by way of the central control facility, which may be centrally located.

In one alternative embodiment, the capture device may include a plurality of position capturing facilities arranged in a distributed manner in the space and at least one position sensor provided on the object or display facility. Such a position sensor, for example, a 3-axis sensor having three orthogonal coils, may be arranged on the object or display facility. The capture device may communicate with position capturing facilities arranged in a fixed position. The position capturing facilities may be arranged in a distributed manner in the space and may be able, by way of corresponding transmit and receive signals, to capture the spatial orientation of the sensor on the object or display facility, so that the control or regulation facility, which may be centrally located, determines the actual spatial position of the object or display facility, after which control/regulation of the lighting facilities can take place. Such position capturing systems, based on electromagnetic coil systems, are adequately known.

In one embodiment, the capture device may include at least one transmit element arranged on the object or display facility, which emits a directed transmit signal, and a receiver element on the one or on each lighting facility. The brightness and/or position of the one or each lighting facility may be controlled or regulated as a function of the captured radiation intensity. The transmit element arranged on the display facility may communicate with a receiver element arranged on the lighting facility, which receives the transmit signals emitted in a directed manner by the transmit element. Each receiver element may determine its relative position to the transmit element from the intensity or level of the received signal. When the receive element and transmit element are directly opposite one another, the receiver element will determine a maximum transmit signal, showing that if lighting were to be provided by way of this lighting facility the light would strike the object or display surface vertically. However, when the transmit element and the receiver element are at an angle to one another, the level of the received signal is lower, it being possible to determine the angle offset again from the level, from which it can again be calculated whether there is the possibility of glare and if it is necessary to vary the brightness and/or position of the relevant lighting facility. As a result, every lighting facility may have a separate control or regulation facility, which controls the change in the brightness and/or position of the associated lighting facility automatically as a function of the captured receiver element signal. However, each receiver element may transmit a receive signal to a central control or regulation facility, which then determines a corresponding adjustment and activates the respective lighting facility.

The transmit element may emit an invisible light, so that it does not itself cause glare. It would be possible to deploy an infrared light transmit element. Alternatively, a transmit element may emit ultrasound signals.

In one embodiment, one or a plurality of transmit elements may be arranged on a frame of the object or display facility. The transmit element(s) is/are arranged in an integrated manner on or in the frame. Direct communication is possible between the transmit elements and the receiver elements. Alternatively, the one or more transmit elements may be integrated, for example, in a unit suspended from the stand.

In one embodiment, the capture device may include at least one sensor facility arranged on the object or display facility, serving to capture an identification signal transmitted by the lighting facility. This sensor facility, which may be integrated on or in the frame, for example, of the display facility, is able to identify immediately the identification signal transmitted by the lighting facility which lighting facility is causing the glare. One benefit of the directed signal transmission and/or the signal capturing restricted by the capturing range is that only the information signal of a lighting facility that is actually in a position that might result in glare is captured. Signals of other lights are not captured. The brightness and/or position of the relevant lighting facilities is/are then changed, to reduce or avoid glare. The brightness/position of lighting facilities that are not involved may remain essentially unchanged but equally their brightness can be increased to some extent, to avoid any loss of brightness in the area to be illuminated.

The identification signal may be transmitted by pulsing of the lighting facilities in a manner that is not visible to the observer. The sensor facility may use the resulting very fast and ultimately infinitesimally small changes in brightness and the resulting pulse pattern to identify the corresponding lighting facility, so that the assigned control or regulation facility can then also identify precisely which lighting facility is involved and should be activated. It would however also be possible to transmit another identification signal by way of an appropriate transmit element, which communicates with the sensor facility, which then has an appropriate receive element.

Various communication options are possible between the mutually communicating components of the inventive examination or treatment facility. A central control or regulation facility may communicate wirelessly with the lighting facilities and/or sensors or sensor facilities arranged on the stand or display facility or the position capturing facilities. However, wired communication may be possible, although this would involve a higher outlay. Wireless communication is possible, for example, based on radio, ultrasound, infrared or Bluetooth. With wireless communication each component of course has corresponding transmit or receiver elements to allow such communication.

The facility may only comprise one monitored lighting facility but generally a plurality of lighting facilities arranged in a distributed manner are provided for optimum illumination or lighting of the object, e.g. a vehicle or any electronic object/television, mobile phone, etc.) or the workstation of the medical facility.

DETAILED DESCRIPTION

The exemplary embodiments that follow describe the invention in the form of a medical examination or treatment facility but apply equally to the embodiment of another type of facility, for example to present objects.

Figure 1:
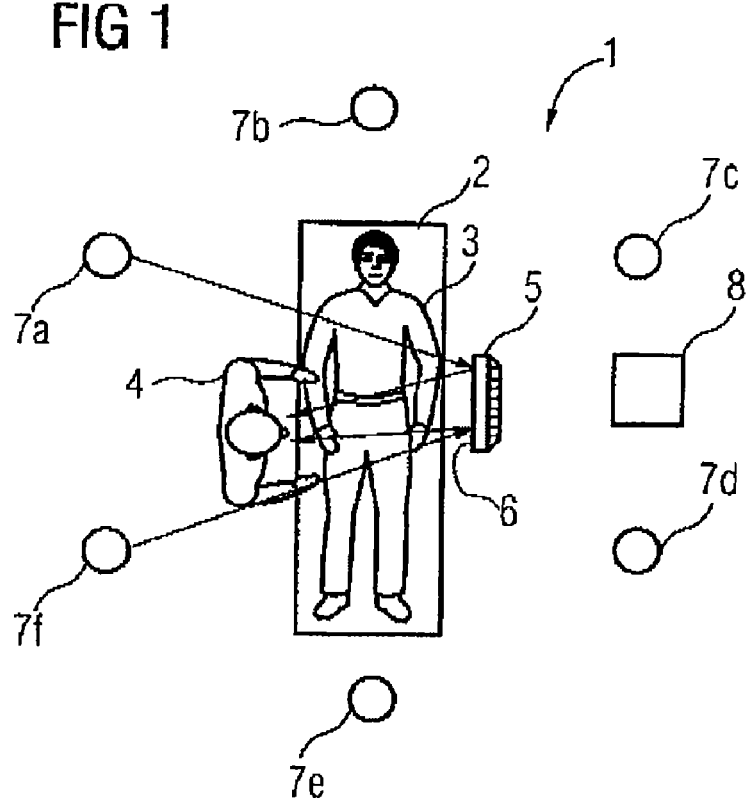
FIG. 1 shows a basic diagram of an inventive medical examination or treatment facility, in which all the lighting facilities are switched on, FIG. 2 shows the examination or treatment facility from FIG. 1 with two lighting facilities whose brightness has been changed.

FIG. 1 shows a medical examination or treatment facility 1. The examination or treatment facility 1 may be any facility, for example, an x-ray or ultrasound facility, although this does not exclude other possibilities. For the sake of clarity FIG. 1 only shows one patient support table 2 with a patient 3 thereon. FIG. 1 also shows a user 4, for example, a physician or other medical personnel, wishing to examine or treat the patient 3. FIG. 1 also shows a display facility 5, for example, a display unit (e.g. LCD display, etc.), which can be moved in space and is supported on the ceiling for example by way of an articulated stand. The user 4 is able to move the display facility 5 in space and orient the display facility 5 so that said user has an optimum view of the display surface 6, in order to be able to see the medically relevant information displayed there (for example, images recorded by way of an ultrasound device or by way of an x-ray facility).

It also shows six separate lighting facilities 7a-7f, the operation of which can be activated separately by way of a control or regulation facility 8 that is central in the example shown. It is possible to change the brightness or the position or both the brightness and position of any individual lighting facility 7a-7f in this process by way of the control facility 8. The brightness can be changed by dimming, for example, continuously between maximum brightness and minimum brightness or switching off the lighting facilities. The position of the pivotable lighting facilities (preferably pivotable through a defined pivot angle in any direction by way of a ball joint) can be adjusted by an appropriate positioning device (e.g., motor with assigned movement mechanism).

The brightness and/or position may be changed in such a manner as to avoid reflection of the light emitted by one or a plurality of lighting facilities off the display surface 6 of the display facility 5. The lighting facilities 7a-7f can be arranged on the ceiling. It is assumed below that the lighting facilities are mounted on the ceiling. However, the lighting facilities 7a-7f do not need to be arranged on the ceiling.

Based on the diagram in FIG. 1, the lighting facilities 7a-7f are oriented so that they illuminate the patient table 2 in an optimum manner, so that the user 4 always has optimum light when treating the patient. Because of the orientation of the essentially vertical display facility 5, the lighting facilities 7a and 7f cause a reflection of the light emitted by the lighting facilities off the display surface 6, so that the user 4 is dazzled and is not able from time to time to see the displayed information or the examination or treatment region of the patient in an optimum manner or at all. This situation is captured by a capturing device for capturing the position and/or orientation of the display facility 5 or its display surface 6 in space and the brightness and/or position of individual lighting facilities involved. The position and/or orientation of the display facility 5 or its display surface 6 in space and the brightness and/or position of individual lighting facilities may be changed automatically, as a function of this capture result, in order to reduce or eliminate the reflection and therefore the glare.

Figure 2:
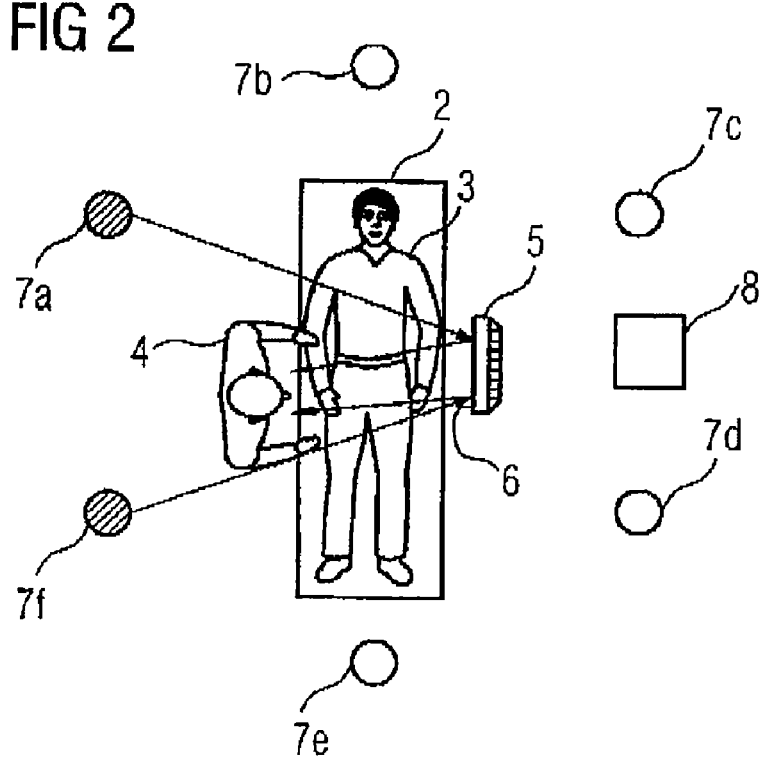

The principle of the function is illustrated in the following FIGS. 2 and 3. As described above, a reflection or glare effect results from the operation of the lighting facilities 7a and 7f, as shown by the arrows. As shown in FIG. 2, once this reflection or glare has been captured automatically, these have been activated in such a manner that their brightness is reduced, in other words they are dimmed or even switched off if the glare is too great, as shown in FIG. 2 by the fact that these lighting facilities 7a and 7f are shown shaded. The brightness and position of the other lighting facilities 7b-7e can remain unchanged but it would also be possible to increase the brightness, particularly of the lighting facilities 7b and 7e, to compensate at least partially for the loss of brightness due to the dimming of the lighting facilities 7a and 7f. As a result of the dimming or switching off of the lighting facility 7a and 7f, the reflection, which was still present in FIG. 1, is reduced or avoided, so that the user 4 no longer has problems when viewing the display surface 6.

Figure 3:
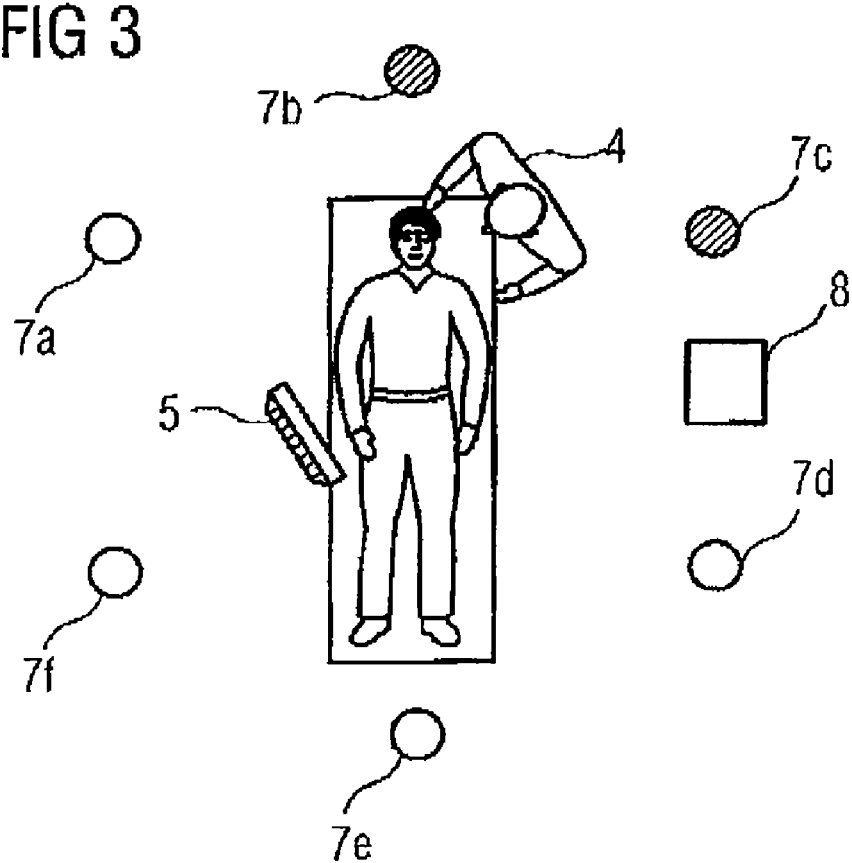
FIG. 3 shows the examination or treatment facility from FIG. 2 with a display facility whose position has been changed and lighting facilities that have been activated in a changed manner.

During the further course of the examination or treatment, the user 4 changes position, as shown in FIG. 3. In order to be able to view the display facility optimally in this position too, the user 4 adjusts the display facility in space, as shown in FIG. 3. This change in the spatial position or orientation of the display facility 5 may be captured automatically and transmitted to the control facility 8, which then resumes operation of the lighting facilities 7a and 7f. Due to the adjustment of the display facility 5, the two lighting facilities 7a and 7f can no longer dazzle. However, glare is possible by the lighting facility 7b and 7c, which is again captured automatically. The brightness and/or position of these two lighting facilities is/are now changed by the control facility 8. The brightness can be dimmed or they can be switched off, as shown in FIG. 3, again by the shading. The brightness of the remaining lighting facilities 7a and 7d-7f may be increased to some extent, in order to compensate for the loss of brightness.

Figure 4:
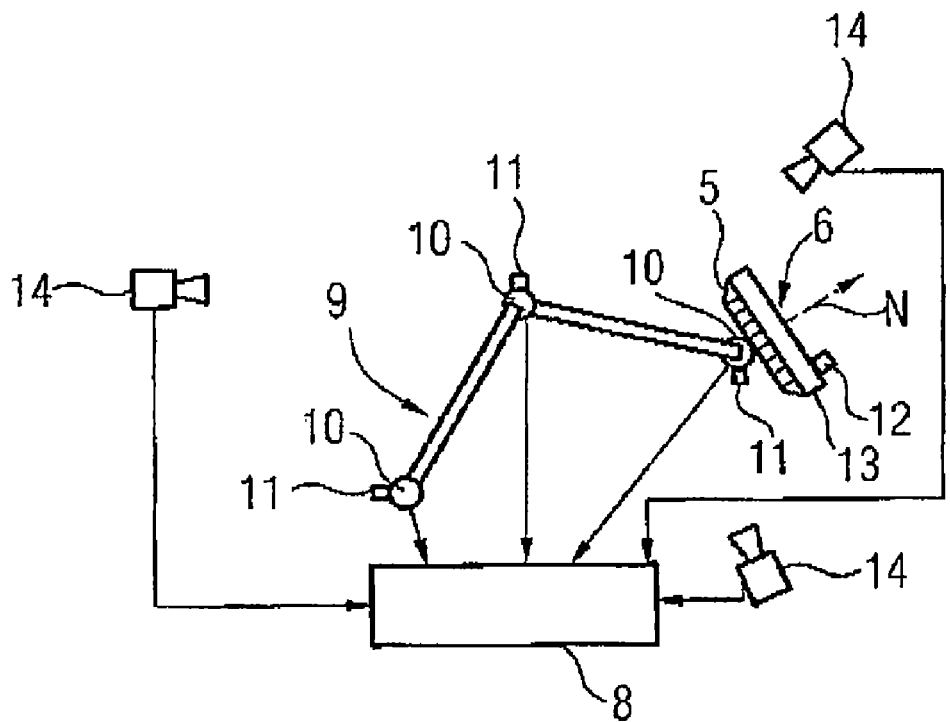
FIG. 4 shows a basic diagram of the capturing of the spatial position and/or orientation of the display facility by way of the geometry of a stand.

FIG. 4 shows a first possibility for capturing the position and/or orientation of the display facility 5 in space. In the example shown, a capture device is supported by a stand 9, it being possible for such a stand 9 to be arranged on the ceiling or to be secured to another component of the facility. Sensors 11 are arranged on the joints 10 (swivel or ball joints) of the stand 9, to capture translatory and/or rotary movements, in other words adjustments about the joints. The display facility 5 is also connected in a movable manner to the stand 9 by a corresponding joint 10, so that it is also supported in a pivotable manner. The sensors 11 communicate with the control or regulation facility 8, so that the facility 8 has the corresponding information. This can now be used to capture the actual spatial position of the display facility 5 or display surface 6. Once the normal vector N of the of the display surface 6 is known, and once the spatial position of the individual lighting facilities, which are arranged in a fixed position as described and whose angular position can be changed as a maximum, is known, it is then possible to determine precisely whether one of the plurality of lighting facilities is contributing to possible glare and reflection.

As an alternative to capturing using sensors arranged on the stand, a position capturing system is also shown. The position capturing system may include a position sensor 12, which is arranged on the frame 13 of the display facility 5. A number (plurality) of position capturing facilities 14 are distributed in space and are able to capture the spatial position and orientation of said position sensor 12. The plurality of position capturing facilities 14 may communicate in turn with the control or regulation facility 8, which can then use the information provided to determine the actual orientation. Cameras may be used as the position capturing facility 14, recording the stand 9 and display facility 5 in the form of images, with the control or regulation facility 8 evaluating the images and determining the actual position of the display facility 5 in space based on the stand geometry captured in the respective images. A position sensor would then not be necessary.

The precise capturing of the actual spatial position of the display facility 5 and the determination of the normal vector N of the display surface 6 is provided, so that it can be determined precisely based on the known spatial positions of the individual lighting facilities whether and if the lighting facility causes possible glare.

Figure 5:
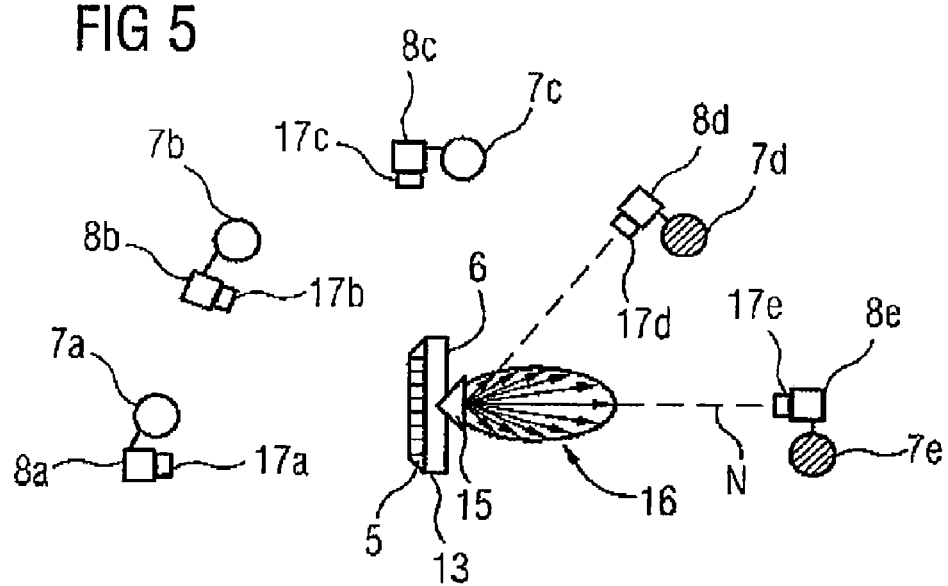
FIG. 5 shows a basic diagram of the capturing of the spatial position and/or orientation of the display facility by way of transmit-receiver communication between the display facility and the lighting facilities and FIG. 6 shows a basic diagram relating to the capturing of the spatial position and/or orientation of the display facility using a sensor facility to capture the identification signals from the individual lighting facilities.

FIG. 5 shows a possibility for capturing the spatial position or orientation of the display facility 5 or display surface 6. To this end a transmit element 15 is arranged on the frame 13 of the display facility 5, transmitting infrared light or ultrasound signals with a defined directional characteristic, for example. This is shown in principle by the individual arrows 16. The five lighting facilities 7a-7f shown here have their own control or regulation facilities 8a-8e, to each of which a receiver element 17a-17e is assigned. The receiver elements 17a-17e serve to capture the radiation emitted by the transmit element 15, which only happens when the transmit element 15 is aligned correspondingly with a receiver element. The receiver elements 17d and 17e are in radiation range of the transmit element 15. The transmit element 15 and the receiver element 17d are oriented directly toward one another, for example, the receiver element 17e stands directly on the normal vector N. The receiver element 17e captures the maximum radiation intensity, compared with the receiver element 17d, which is at an angle to the normal vector N. The receiver element 17e captures significantly less radiation emitted by the transmit element 15. The higher the detected radiation intensity, the closer the respective receiver element 17a-17e and therefore the assigned lighting facility to the normal vector and the higher its glare factor would be.

The receiver elements 17a-17c do not receive any radiation emitted by the transmit element 15. As a result, the operation does not have to be varied. It is different for the lighting facilities 7d and 7e, however, the amount of glare of the lighting facility 7e being considerably greater because of its direct perpendicular orientation to the display surface 6 than that of the lighting facility 7d. In any case the respective brightness is now varied by way of the lighting facility's own control or regulation facilities 8b and 8e, as shown by the shading of the lighting facilities 7d and 7e. Adjustment of the position of the lighting facility 7d and 7e would also result in an improvement.

In the case of a spatial adjustment of the display apparatus 5, the captured radiation intensity of the individual receiver elements may be changed, depending on which receiver element is then being correspondingly acted on, so that the corresponding activation of the individual lighting facilities then also necessarily changes.

Figure 6:
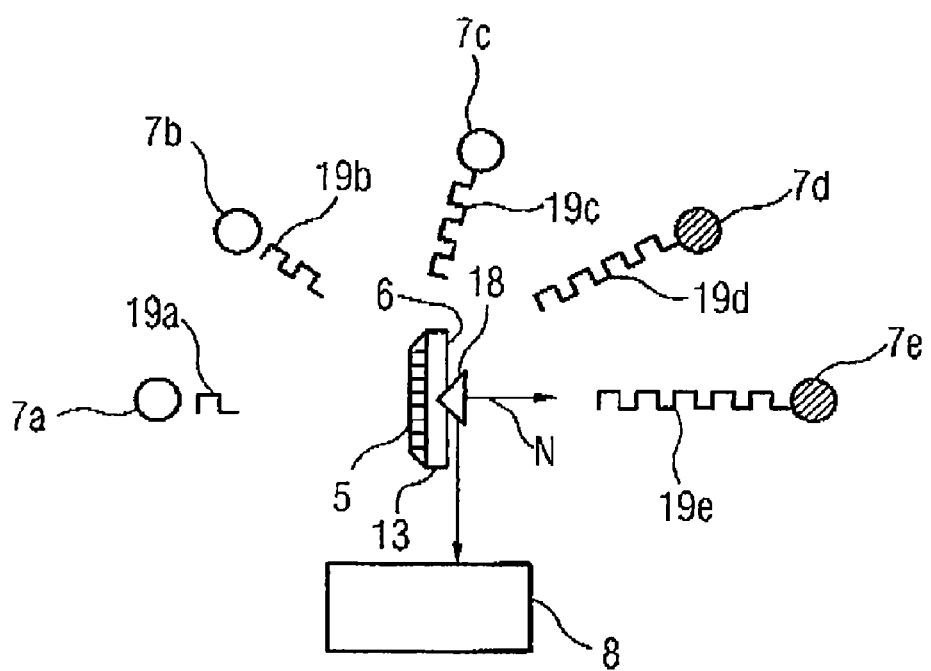

FIG. 6 shows a further embodiment of the capturing of the spatial position and/or orientation of the display facility 5. A sensor facility 18 is also present on the frame 13, serving to capture an identification signal transmitted by the respective lighting facility 7a-7e and identifying the individual lighting facility. Each lighting facility 7a-7e is able to transmit an identification signal 19a-19e. This can be done, for example, by sufficiently high-frequency pulsing of the emitted light, resulting in a corresponding varying brightness signal at the sensor facility 18. The individual identification signals 19a-19e are shown with correspondingly different lengths of individual pulse signals.

The sensor facility 18 is now able to capture the respective identification signal 19a-19e of those lighting facilities, which is present within its restricted, directed capture range. The lighting facility 7e here is also diametrically opposite the display facility 5, so that the sensor facility 18 captures the identification signal 19c, with the result that the control facility 8 identifies directly that regulation of the brightness and/or position of the lighting facility 7e is necessary to avoid glare, as shown by the shading. The lighting facility 7b, which radiates at an angle to the normal vector onto the display surface 6 also contributes to glare to a certain extent. The sensor facility 18 captures the identification signal 19b, which is still within the capture range. The control or regulation facility 8 identifies from the identification signal 19d that the lighting facility 7d also contributes to the glare and varies the brightness and/or position. The other identification signals may not be captured, as they are outside the capture range. If the display facility is adjusted, the capture range is also adjusted, so that other identification signals are then captured in some instances and the lighting facilities defined by these are identified as causing glare. The position/orientation of the display facility is thus determined by way of directed capturing of the identification signal.

Instead of pulsing the lighting facility or lighting device, a separate identification signal transmit element may be provided at each lighting facility 7a-7d, to transmit the identification signal. It is also possible to arrange a plurality of sensor facilities 18 on the frame.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:
1. A system comprising:
at least one display system comprising a screen, the at least one display system being movable in a space, the screen being configured to display an image, one or more lighting facilities arranged in a distributed manner to illuminate the space, and a control system that is operable to automatically change a brightness, a position, or the brightness and the position of the one or more lighting facilities as a function of a captured spatial position, a captured orientation, or the captured spatial position and the captured orientation of the at least one display system.

2. The system of claim 1, wherein the control system is a central control system, the central control system being operable to control or regulate the one or more lighting facilities.

3. The system of claim 1, wherein the control system is operable to automatically change the brightness of the one or more lighting facilities, and
wherein the brightness is changeable continuously or in discrete intervals between a maximum brightness and a minimum brightness or a switched-off state.

4. The system of claim 1, wherein a position of a lighting facility of the one or more lighting facilities that is pivotable is adjustable continuously or in discrete intervals.

5. The system of claim 1, further comprising a capture device that is operable to automatically capture the spatial position, the orientation, or the spatial position and the orientation of the at least one display system.

6. The system of claim 5, wherein the capture device is configured based on a spatial geometry of a support or a stand holding the at least one display system.

7. The system of claim 6, further comprising one or more sensors for capturing a translatory stand movement or a rotary stand movement, the one or more sensors being provided on the support or the stand.

8. The system of claim 5, wherein the capture device includes a plurality of position capturing facilities arranged in a distributed manner in space.

9. The system of claim 5, wherein the capture device includes:
at least one transmit element arranged on the at least one display system, the at least one transmit element emitting a directed transmit signal, and
a receiver element on each lighting facility of the one or more lighting facilities, the brightness, the position, or the brightness and the position of the lighting facility being controlled or regulated as a function of a captured radiation intensity.

10. The system of claim 9, wherein a transmit element of the at least one transmit element is a transmit element emitting invisible light or a transmit element emitting ultrasound.

11. The system of claim 9, wherein one or more transmit elements of the at least one transmit element are arranged on a frame of the at least one display system.

12. The system of claim 5, wherein the capture device comprises at least one sensor arranged on the at least one display system, the at least one sensor capturing an identification signal transmitted by the one or more lighting facilities.

13. The system of claim 12, wherein the at least one sensor is provided on a frame on the at least one display system.

14. The system of claim 1, wherein a central control or regulation facility communicates wirelessly with at least one of the one or more lighting facilities, sensors or sensor facilities arranged on a support or a stand holding the at least one display system, the at least one display system, and position capturing facilities.

15. The system of claim 1, wherein each lighting facility of the one or more lighting facilities comprises a control system.

16. The system of claim 6, wherein the capture device is configured based on a spatial geometry of an articulated stand.

17. The system of claim 8, further comprising at least one position sensor provided on the at least one display system.

18. The system of claim 10, wherein one or more transmit elements of the at least one transmit element are arranged on a frame of the at least one display system.

19. A system comprising:
a display system that is movable in a space,
one or more lighting devices arranged in a distributed manner to illuminate the space,
a capture device operable to automatically capture a spatial position, an orientation, or the spatial position and the orientation of the display system, and
a control system that is operable to automatically change a brightness, a position, or the brightness and the position of the one of more lighting devices as a function of the captured spatial position, the captured orientation, or the captured spatial position and the captured orientation of the display system,
wherein the capture device comprises a sensor arranged on the display system, the sensor being configured to capture an identification signal transmitted by the one or more lighting facilities.

* * * * *